(12) United States Patent
Hyde et al.

(10) Patent No.: US 6,957,098 B1
(45) Date of Patent: Oct. 18, 2005

(54) MARKERS FOR INTERVENTIONAL DEVICES IN MAGNETIC RESONANT IMAGE (MRI) SYSTEMS

(75) Inventors: Gregory Matthew Hyde, Menlo Park, CA (US); Christian Jason Landry, Sugar Land, TX (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 471 days.

(21) Appl. No.: 10/184,531

(22) Filed: Jun. 27, 2002

(51) Int. Cl.[7] ............................. A61B 5/05; A61M 1/00
(52) U.S. Cl. ....................................... 600/424; 604/540
(58) Field of Search ................................ 600/424, 407, 600/524; 604/540, 541, 542, 543, 544; A61B 5/05; A61M 1/00

(56) References Cited

U.S. PATENT DOCUMENTS 5,840,024 A * 11/1998 Taniguchi et al. .......... 600/424
6,059,718 A * 5/2000 Taniguchi et al. .......... 600/117
6,216,027 B1 * 4/2001 Willis et al. ................. 600/424
6,490,474 B1 * 12/2002 Willis et al. ................. 600/424

* cited by examiner

*Primary Examiner*—Daniel Robinson
(74) *Attorney, Agent, or Firm*—Blakely, Sokoloff, Taylor & Zafman LLP

(57) ABSTRACT

Methods and apparatuses for locating a catheter, or other medical international devices are described herein. In one aspect of the invention, an exemplary method includes providing a pressure sensitive device attached to a body of a catheter, providing a resonant circuit coupled to the pressure sensitive device in the catheter, the resonant circuit having an oscillating frequency, generating a magnetic field, the magnetic field inducing and causing the resonant circuit to oscillate, applying a pressure on the pressure sensitive device, the pressure applied on the pressure sensitive device changing the frequency of the resonant circuit, detecting the oscillation of the resonant circuit, and determining location of the catheter based on the oscillation of the resonant circuit. Other methods and apparatuses are also described.

15 Claims, 17 Drawing Sheets

MARKERS FOR INTERVENTIONAL DEVICES IN MAGNETIC RESONANT IMAGE (MRI) SYSTEMS

FIELD OF THE INVENTION

The present invention relates generally to the field of a magnetic resonant imaging (MRI) system, and more particularly to markers for an interventional device in an MRI system.

BACKGROUND OF THE INVENTION

For a wide range of medical reasons, medical catheters, medical surgical devices such as therapeutic devices, and electrical sensing and/or stimulation electrode bearing leads are introduced into a patient's body either temporarily or chronically for monitoring and/or therapeutic operations. In many of the medical applications for these devices, it is necessary to precisely locate a structure at or near the distal end of the catheter or lead body in relation to specific body tissue in a body cavity or vessel.

In the magnetic resonant imaging (MRI) industry, active marker detection has become a growing interest. With the powerful magnetic field of an MRI system, a conventional method includes a circuit having an RF coil, a capacitor, and resistor. Such a circuit is attached to the end of a catheter for use in coronary dilation procedures or where guide wire applications are necessary.

Typically, the conventional methods of active marker detection use insulated wires or photo illumination to excite the RLC circuit. However, this method may potentially harm the patient when an insulated wire extends the full length of the catheter or the bulkiness of a detuning photo-resistor may make interventional procedures virtually impossible. Thus a better design and methods are desirable.

SUMMARY OF THE DISCLOSURE

Methods and apparatuses for locating a catheter or other medical interventional devices are described herein. In one aspect of the invention, an exemplary method includes providing a pressure sensitive device attached to a body of a catheter, providing a resonant circuit coupled to the pressure sensitive device in the catheter, the resonant circuit having an oscillating frequency, generating a magnetic field, the magnetic field inducing and causing the resonant circuit to oscillate, applying a pressure on the pressure sensitive device, the pressure applied on the pressure sensitive device changing the oscillating frequency of the resonant circuit, detecting the oscillation of the resonant circuit, and determining location of the catheter based on the oscillation of the resonant circuit.

In one particular exemplary embodiment, the method includes generating a radio frequency (RF) signal through the oscillation of the resonant circuit, detecting the oscillation of the resonant circuit through sensing the intensity of the RF signal, and determining the location of the catheter's distal tip based on signals produced from the RF signal by the resonant circuit.

In yet another aspect of the invention, an exemplary method includes providing a pressure sensitive device and a piezoelectric device attached to a body of a catheter, providing a resonant circuit coupled to the pressure sensitive device and the piezoelectric device in the catheter, the resonant circuit having an oscillating frequency, applying a first pressure on the piezoelectric device, the first pressure applied on the piezoelectric device causing the piezoelectric device to generate a current in and cause the resonant circuit to oscillate, applying a second pressure on the pressure sensitive device, the second pressure applied on the pressure sensitive device changing the resonant frequency of the resonant circuit, detecting the oscillation of the resonant circuit, and determining location of the catheter based on the oscillation of the resonant circuit.

Other methods are described and apparatuses are also described. Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings in which like references indicate similar elements.

DETAILED DESCRIPTION

The following description and drawings are illustrative of the invention and are not to be construed as limiting the invention. Numerous specific details are described to provide a thorough understanding of the present invention. However, in certain instances, well-known or conventional details are not described in order to not unnecessarily obscure the present invention in detail.

Figure 1:
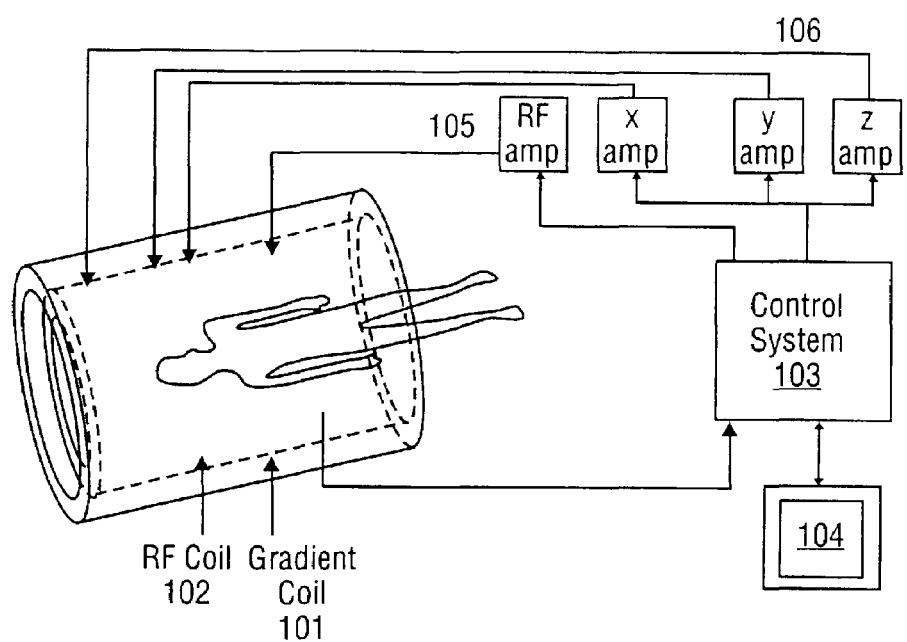
FIG. 1 illustrates a magnetic resonant imaging (MRI) system in the art.

FIG. 1 illustrates a typical magnetic resonant imaging (MRI) system. The MRI system 100 typically includes a magnet to impose the static magnetic field, gradient coils 101 for imposing spatially distributed magnetic fields along three orthogonal coordinates, and RF coils 102 to transmit and receive RF signals to and from the selected nuclei. The signal received by the coil 102 is transmitted to a control system 103 which processes the data into an image displayed on display 104. The magnetic resonance image is composed of picture elements called "pixels." The intensity of a pixel is proportional to the signal intensity of the contents of a corresponding volume element or "voxel" of the object being imaged. The control system 103 also controls the operation of RF coils 102 and gradient coils 101 through the RF amplifier 105 and gradient amplifiers 106, respectively.

When a body is positioned within the magnetic field, its nuclei align with and rotate around the direction of this field. As an RF signal of a hydrogen-specific frequency (in the case where the selected nuclei are hydrogen nuclei) is transmitted through the body, some of the nuclei absorb the RF energy and change direction (or "resonate"). When the RF signal is stopped the nuclei return to their original position, releasing the absorbed energy and generate a signal of their own. This signal is picked up by an RF receiver antenna and processed by the computer into an image.

MR images can provide excellent contrasts and representation of tissue anatomy. The picture produced by the MRI enable the physician to detect and define the differences between healthy and diseased tissue, thus giving a more precise diagnosis. MR's ability to clarify differentiate soft tissues makes it the modality of choice for many procedures-including head, spine, and musculoskeletal studies.

Figure 2:
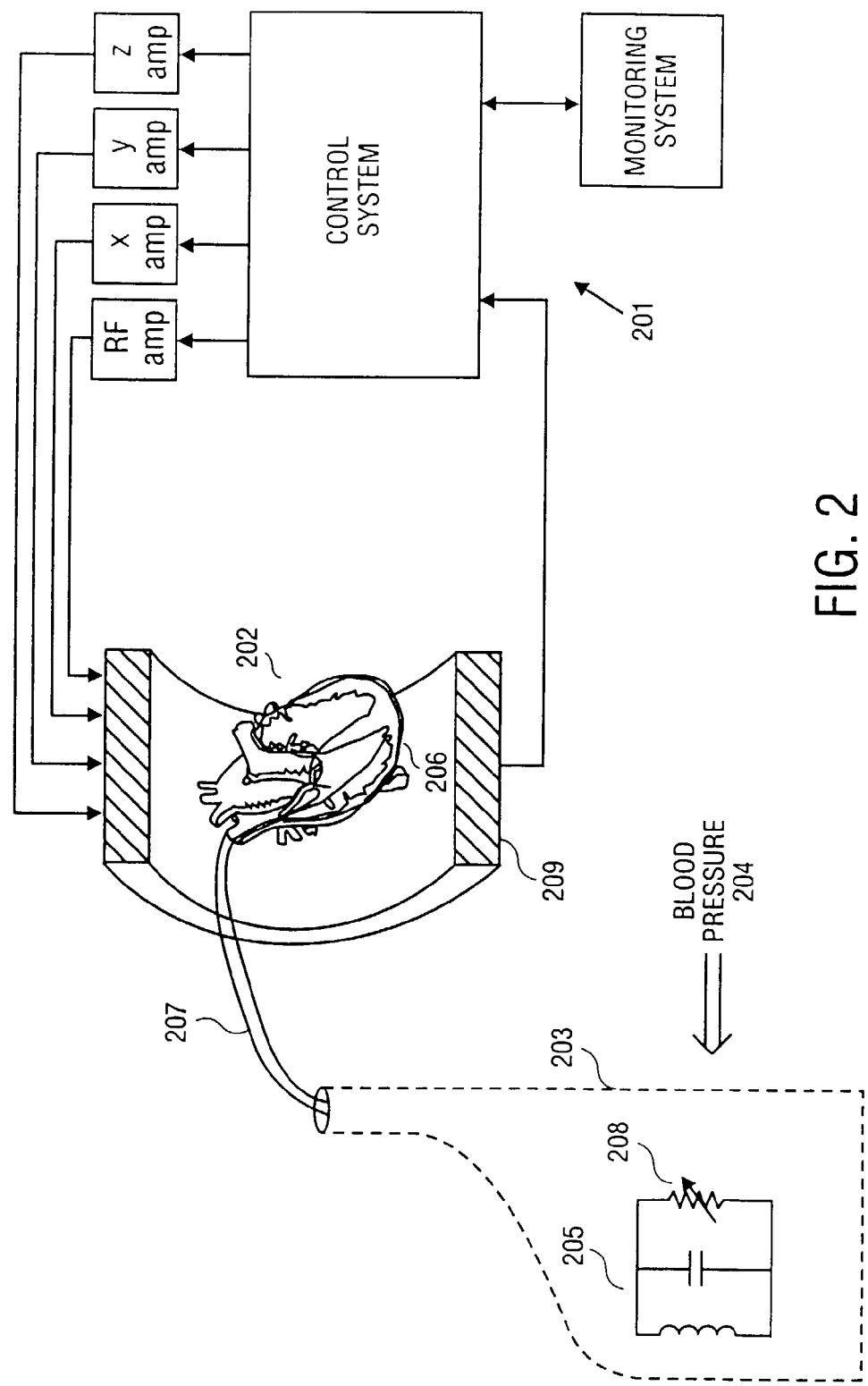
FIG. 2 illustrates a system according to an embodiment of the invention.

FIG. 2 illustrates an embodiment of the invention. The system of FIG. 2 includes an MRI system. The MRI system generates and radiates a magnetic field outside a patient's body at a predetermined resonant oscillating frequency, and receives signals which are processed to produce an image of an internal part (or all) of the patient's body (e.g., human heart 202). The MRI system may be an ordinary MRI system which is well known in the art. In this embodiment, an active marker is constructed in a distal tip region 203 of a catheter 207 for an intervention device. The intervention device may be placed inside the patient's body, such as in a blood vessel 206 of a human heart 202. In one embodiment, the intervention device may be a catheter with an active marker assembly and the catheter has a catheter lumen extending therethrough from a proximal end to a distal end, a pressure sensitive device attached to, for example, the distal end of the catheter, and a resonant circuit coupled to the pressure sensitive device, the resonant circuit having a resonant oscillating frequency. The pressure sensitive device may receive a pressure from an external source, such as a pressure controller coupled at a proximal end of the catheter, or, as shown in FIG. 2, the pressure sensitive device may receive a pressure from the patient's blood pressure (e.g., an internal source near the distal end of the catheter. It would be appreciated that the resonant circuit 205 is embedded in the tip portion of the catheter 207. According to one embodiment, when the catheter is inserted into an internal part of the patient, such as blood vessel 206 of the human heart 202, the resonant circuit embedded in the tip portion of the catheter is placed inside the vessel 206. The dotted portions of the Figures are enlarged for better illustration only.

When the pressure sensitive device 208 receives a pressure 204 from the patient's body (e.g., the patient's blood pressure), the pressure sensitive device 208 determines an oscillating frequency of the resonant circuit 205 coupled to the pressure sensitive device. As a result, the resonant circuit 205 starts to oscillate at a resonant oscillating frequency determined by the values of the components of the resonant circuit. It would be appreciated that the oscillating frequency may be adjusted substantially close to the Larmore frequency used by the MRI system. When the resonant circuit 205 oscillates, it generates a radio frequency (RF) signal having a frequency close to the resonant oscillating frequency of the resonant circuit. The RF signal from the circuit is broadcast and received by the MRI coil 209 and thereafter is transferred to the MRI receiving system 201. As a result, the location of the resonant circuit can be determined using known techniques.

Figure 3A:
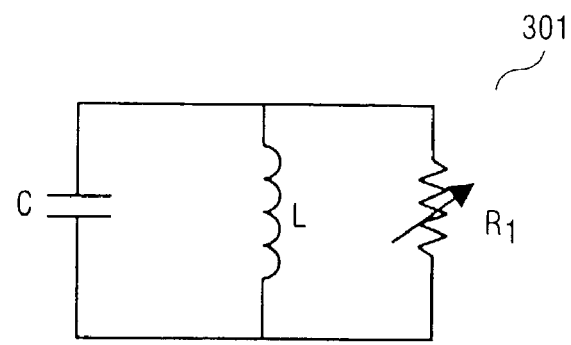
FIG. 3A illustrates a catheter according to an embodiment of the invention.
Figure 3A:
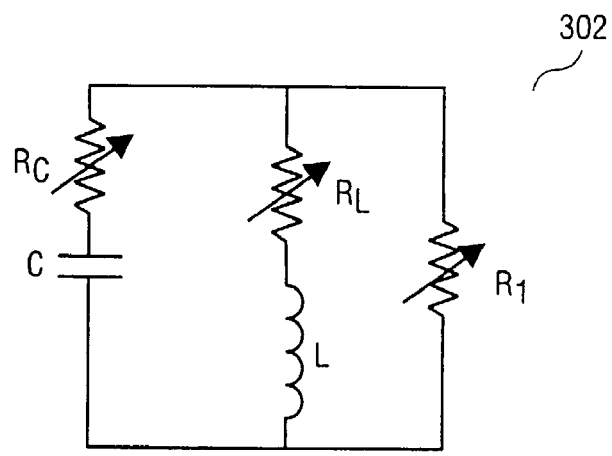
Figure 3A:
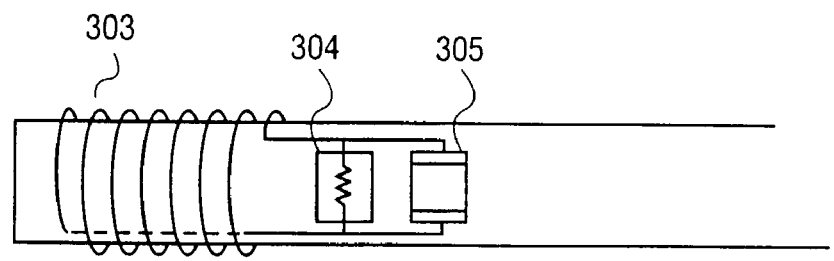

FIG. 3A illustrates an embodiment of a catheter according to an aspect of the invention. The catheter includes a resonant circuit 301 which has an equivalent electrical model 302. In one embodiment, the resonant circuit includes an LC tank circuit. In a particular embodiment, the resonant circuit may include a radio frequency (RF) coil 303, a capacitor 304, and a pressure sensitive resistor 305, which may be utilized at the end of a catheter to make it visible during an MRI while interventional procedures are being performed. The resonant circuit may be activated by changes in the magnetic field, magnetic field gradients or the emitted RF energy produced by the MRI system, such as MRI system 201 of FIG. 2, and various echoing techniques. The high energy field in conjunction with absorption and emission techniques of the MRI system excite the resonant circuit with an RF signal to obtain a tuned RLC circuit to achieve resonance. The RF energy may be emitted by the MRI excited circuit and the emitted RF energy is picked up by an MRI coil.

One of the advantages of the embodiment is that this is done without any excitation of the RLC circuit from an external source other than an ordinary MRI system. The resonance can be visible in an MRI application by a generated RF signal effect of the object at the position where the RLC circuit is in a catheter, typically in a distal tip region of the catheter. In one embodiment, when an RF signal is generated from the resonant circuit located at the distal end of the catheter, the RF signal is received by the MRI receiving system and displayed as a bright spot while the rest of the image remains relatively darker. As a result, the location of the distal end of the catheter may be determined. This process is also called masking effect. When this masking effect is eliminated periodically and over laid with a non-masking image at the same position on the catheter, a precision marker could be seen, as the resonant frequency is turned on or off, similar to a flashing image. However, if the resonant circuit could be turned off, the masking would be eliminated and when coupled with a non-masked image an object such as a marker could be seen during intravascular procedures. The non-masking techniques may be accomplished by detuning the resonant circuit. The detuning is accomplished by changing the value of the resistor thus changing the resonant frequency of the RLC circuit. By using the pressure sensor in the resonant circuit, the value of the resistor would change as the blood pressure changes with every heartbeat (or by otherwise changing the pressure, such as, for example, through a pressure controller which is coupled to a proximal end of the catheter). This technique, coupled with the MRI echoing techniques to cycling the resonant oscillating frequency on and off, would allow for an optimal image of a catheter and its markers.

The parameters of the resonant circuit may be adjusted such that the resonant oscillating frequency is set substantially close to the resonant oscillating frequency of an MRI system. The pressure sensitive device may be a pressure sensitive resistor, which resistance changes based on the pressure received. In a case that the resonant circuit is an LC tank circuit with a pressure sensor resistor, the resonant oscillating frequency is determined by the value of the inductor, capacitor, and their respective impedances. The impedance of the circuit is determined by the effective inductor and capacitive impedance, and in this case, the impedance will be effected by the pressure sensor resistor. The resonant oscillating frequency may be described as follows:

$$fr = \frac{1}{2\pi\sqrt{LC}} \sqrt{\frac{L - CR_L^2}{L - CR_C^2}}$$

Where the L is inductance and C is capacitance, of the circuit. This equation shows that in the circuit of FIG. 8, the resonant frequency can be tuned or detuned by varying the resistance in one of the branches. In this case, the impedance of inductor $R_L$, may be described as follows:

$$R_L = \sqrt{\left(\frac{X_L}{X_C}\right)R_C^2 - X_L^2 + \left(\frac{L}{C}\right)}$$

Where the $R_L$ is effective resistance of the inductor. The same is true for the effective resistance of the capacitor of FIG. 8. $X_L$ and $X_C$ are the inductive and capacitive reactance. Inductive reactance increases with an increase in frequency and capacitive reactance decreases with an increase in frequency. Both $X_L$ and $X_C$ make up the resistances for the capacitor and the inductor branches of the parallel resonant circuit. By varying the effective resistance of C, in this case, the circuit can be tuned or detuned in and out of resonance.

An embodiment of the invention calculates the impedance of the RLC circuit at resonance and allows the circuit to enter a resonant state. Once the circuit enters the resonance state, pressure is applied to increase or decrease resistance that would match or come close to the impedance of either the $R_C$ or $R_L$, which tune or detune the circuit's resonant frequency. By controlling the pressure, it is possible to tune or detune the circuit and cause a corresponding change in the MRI image (e.g., change the image from one showing the marker to another which does not show the marker).

Figure 3B:
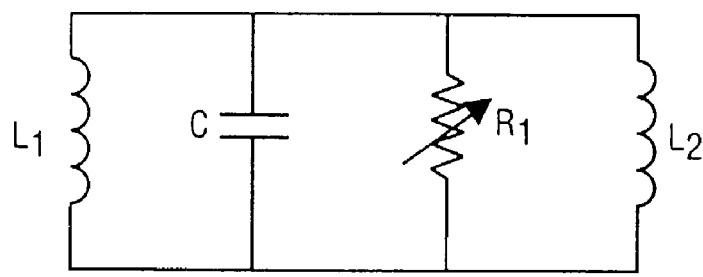
FIG. 3B illustrates an alternative catheter according to an embodiment of the invention.
Figure 3B:
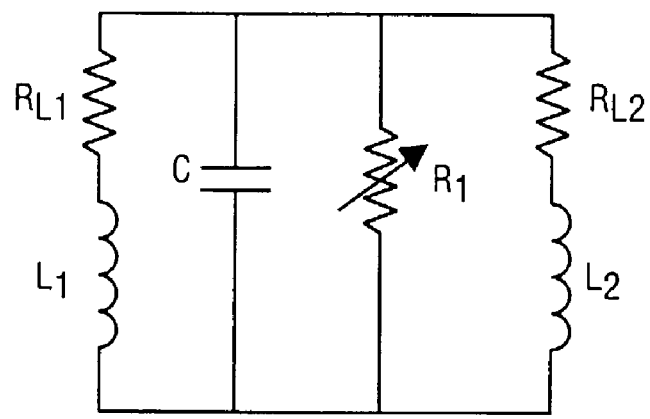
Figure 3B:
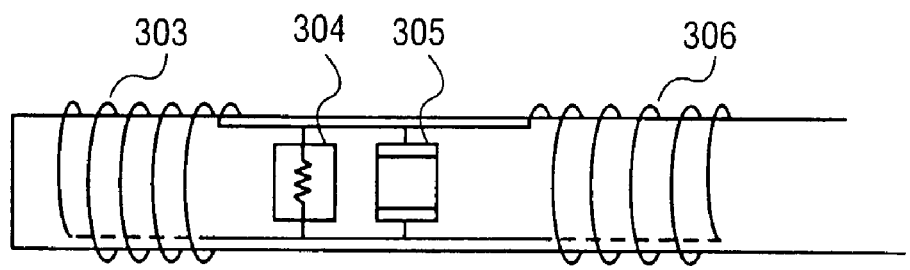

FIG. 3B illustrates an alternative embodiment of the invention. The catheter of FIG. 3B includes a first inductor coil 303 and a second inductor coil 306, as well as capacitor 305 and a pressure sensitive resistor 304, to form a multiple marker catheter. It would be appreciated that multiple inductor coils may be implemented to form a multiple marker catheter.

Figure 4:
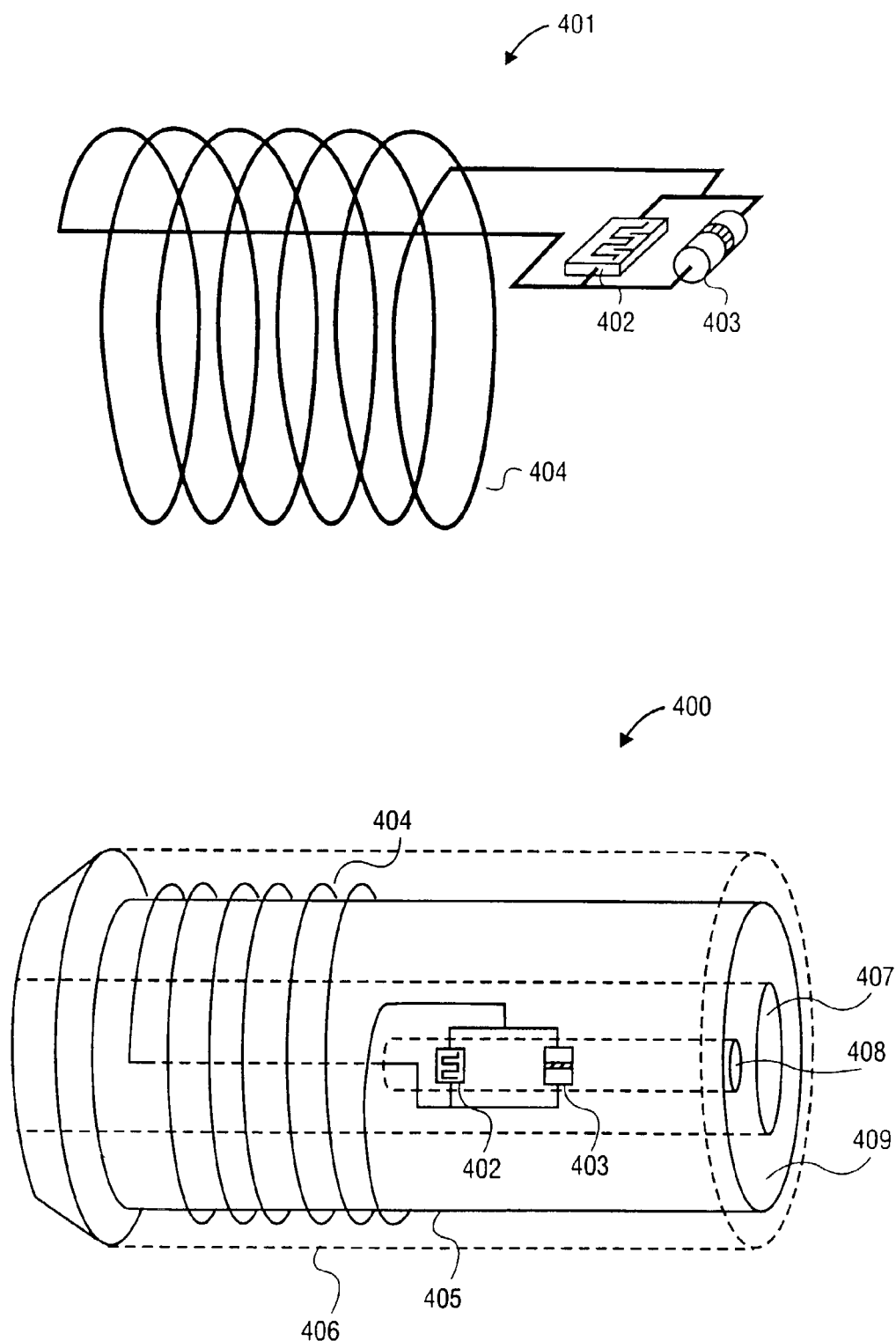
FIG. 4 illustrates an alternative catheter according to an embodiment of the invention.

FIG. 4 illustrates another alternative embodiment of a catheter with a resonant circuit built therein. In this embodiment, an LC tank circuit with a pressure sensor resistor 402 is used as a resonant circuit. The pressure sensor 402 may be a miniature pressure sensor for in-vivo measurement of blood pressure. Referring to FIG. 4, the catheter includes an outer member 406 and an inner member 405. The inner member 405 includes a pressure lumen 408, in which a pressure is transmitted to the pressure sensitive resistor 402. The inner member 405 also includes a guide wire lumen 407 where a guide wire may be inserted therethrough. Alternatively, the pressure sensitive resistor 402 may receive pressure from a blood pressure, such as blood pressure 204 from a human heart 202 of FIG. 2. The catheter may include other lumens depending on the use of the catheter, such as inflation lumens (e.g. to inflate an angioplasty balloon or to inflate a centering balloon for some treatment such as a radiation or drug treatment), or a drug delivery lumen to introduce a drug to a coronary site, or a perfusion lumen to allow perfusion of oxygenated blood to sites; downstream from the site of the catheter's distal end.

In one embodiment, the miniature pressure sensing resistor may be attached to the catheter in a subminiature substrate form and doped, attached with adhesive to the outer wall of the catheter tubing. In an alternative embodiment, the miniature pressure sensing resistor may be incorporated into the wall of the tubing 409. The outputs of the miniature pressure sensing resistor may be coupled to the capacitor and inductor micro coil, in parallel as shown in FIG. 3A. The micro coil 404 may be wound around the catheter in a fashion which facilitates a maximum Q factor. In one embodiment, the capacitor 403 may be a small surface mount capacitor well known in the art. In an alternative embodiment, the capacitor 403 may be fashioned as part of the tubing wall or well of the catheter.

Alternatively, as illustrated in FIG. 3B, more than one inductor coils may be wound around the catheter tubing to form a multi-marker catheter. The multi-marker configuration may be electrically wired the same as the single micro coil circuit, but preferably separated by the series capacitor which is in parallel with the miniature pressure sensing resistor. Either micro coil configuration, once applied to the catheter tubing, may have outer tube encasing it to prevent contamination or any ill effects upon vessel walls.

Figure 5A:
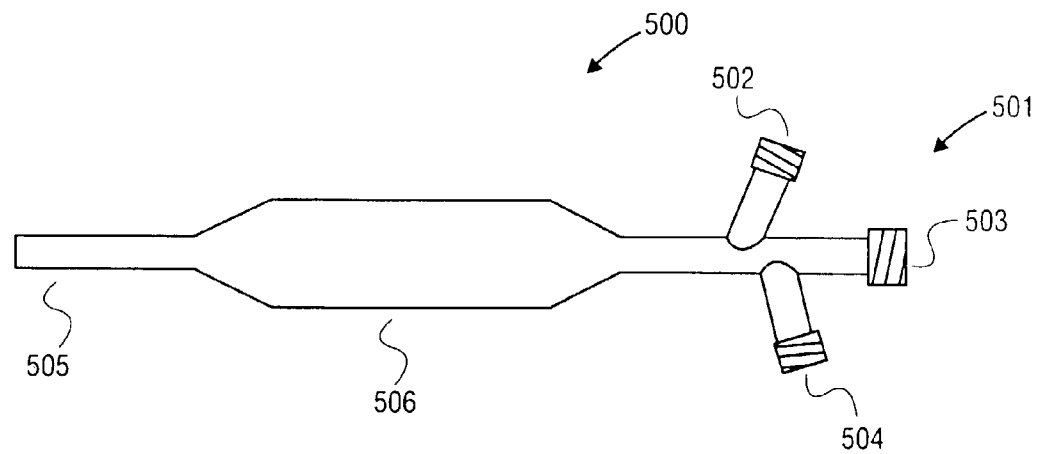
FIG. 5A illustrates an alternative catheter according to an embodiment of the invention.
Figure 5A:
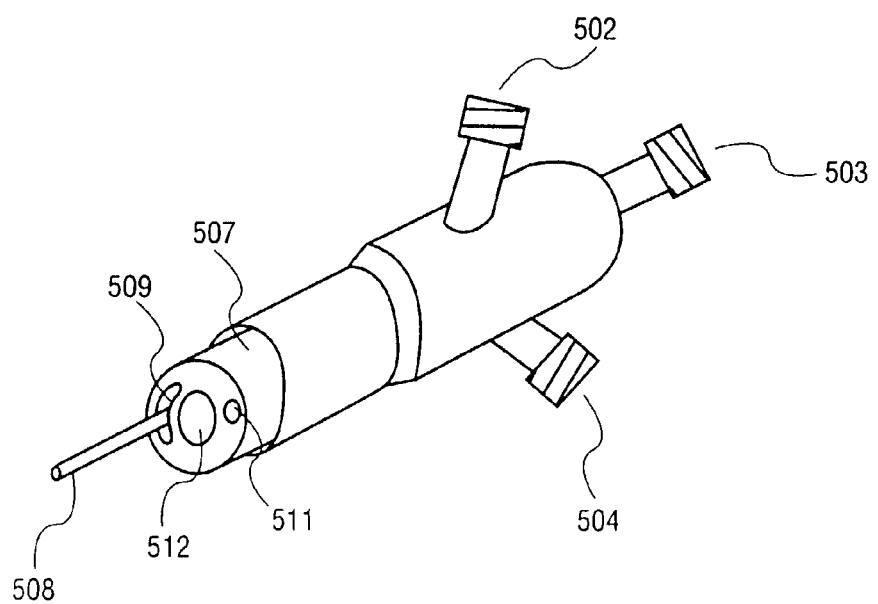

FIG. 5A illustrates a catheter according to yet another alternative embodiment of the invention. The catheter 500 includes a proximal end 501, a distal end 505, and a balloon 506. The proximal end 501 includes an inflation port 502 which may be used to inflate the balloon 506. The proximal end 501 also includes a hydraulic control port 504, where a hydraulic pressure may be transmitted through the hydraulic port 504 and applied to the pressure sensitive resistor, such as pressure sensitive resistor 402, through a pressure lumen 408 of FIG. 4. The distal end may be construed to include an LC resonant circuit and a pressure sensing resistor, as described at distal tip region 400 of FIG. 4. In this embodiment, the catheter may include an annular space 507 for balloon inflation, a support mandrel lumen 509, where a support mandrel 508 is extended therethrough. A guide wire lumen 512 is located inside the catheter 500 extended from the guide wire port 503. Similarly, a hydraulic pressure lumen 511 is extended from the hydraulic control port 504. The hydraulic control port 504 may be coupled to a pressure controller controlling and supplying hydraulic pressure to the pressure sensing resistor attached to the distal end 505. The pressure controller may be coupled to an MRI system, as described in FIG. 6.

Figure 5B:
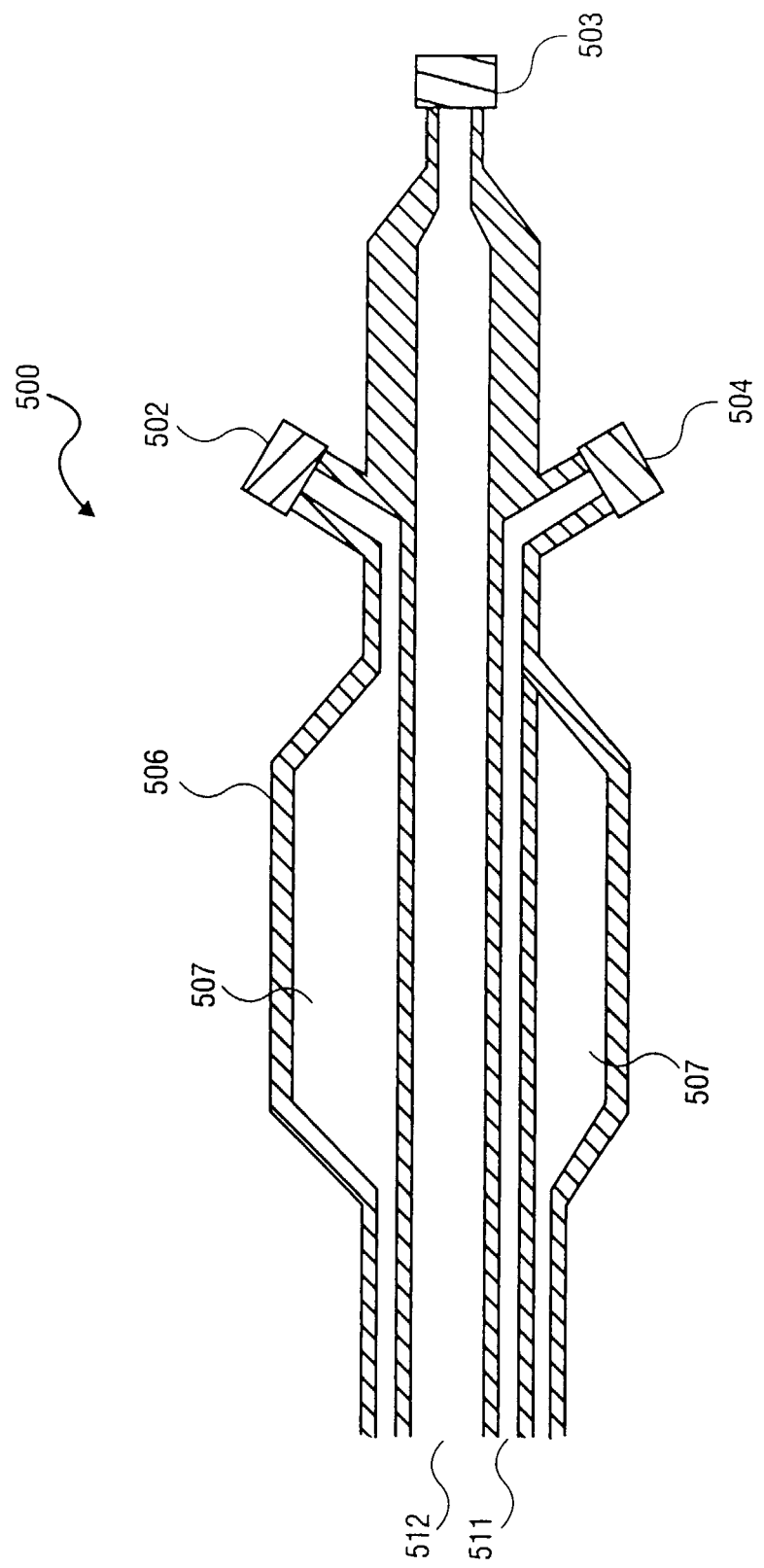
FIG. 5B illustrates an alternative catheter according to an embodiment of the invention.

FIG. 5B illustrates a cross section of the catheter 500 of FIG. 5A. The catheter 500 includes an inflation port 502 for inflating the balloon 506 through the annular space 507. The catheter 500 also includes a hydraulic control port 504, which may be used to transmit hydraulic pressure to the pressure sensing resistor, such as resistor 403 of FIG. 4, through the hydraulic pressure lumen 511. The catheter 500 further includes a guide wire port 503 for a guide wire extended through the guide wire lumen 512. Other configurations may be utilized.

Figure 6:
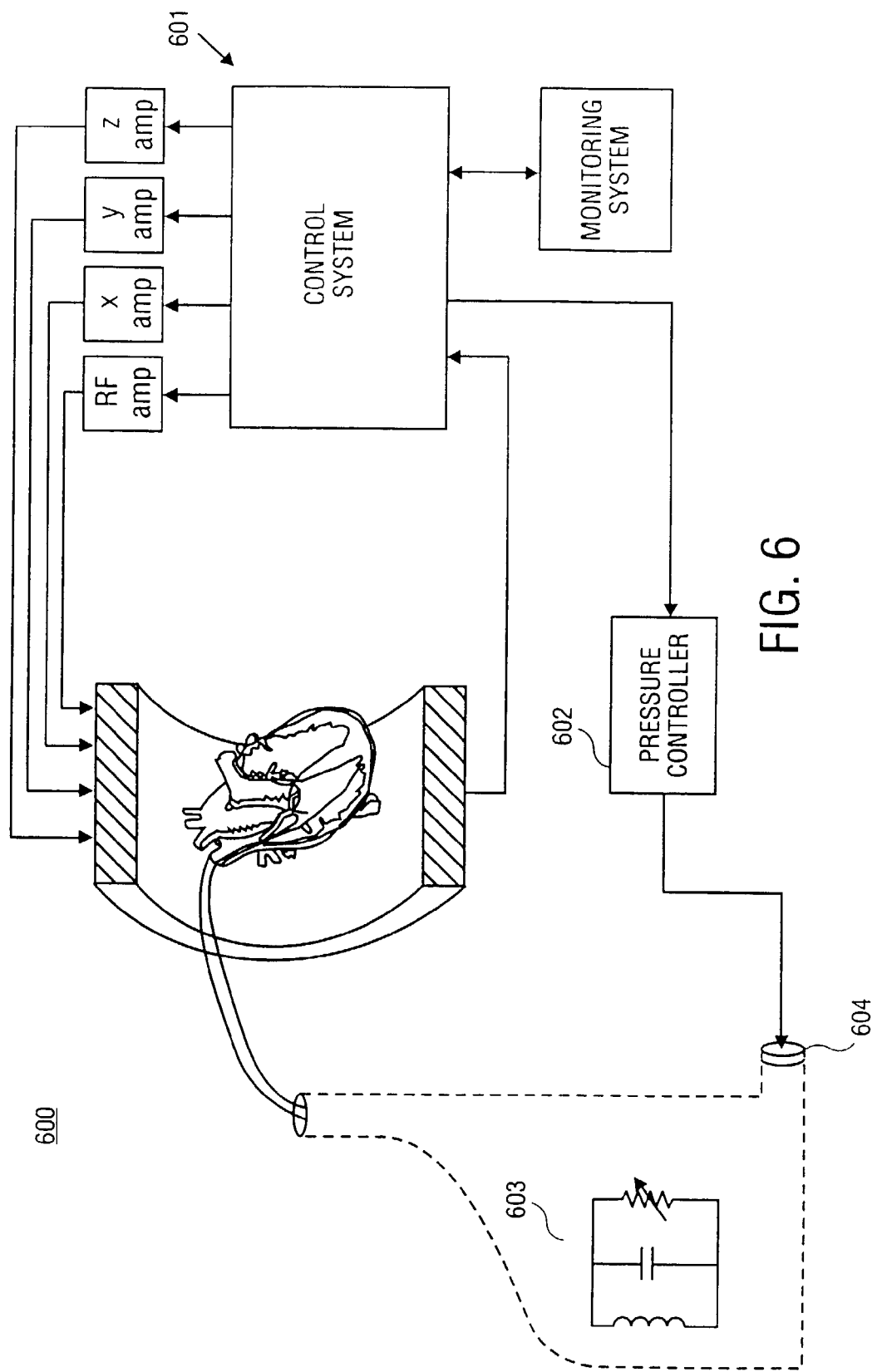
FIG. 6 illustrates an alternative system according to an embodiment of the invention.

FIG. 6 illustrates an alternative embodiment of a catheter with a resonant circuit 603 built therein. The resonant circuit 603 incorporates a micro fabricated pressure sensor as a detuning catalyst. Similar to the RLC resonant circuit above, the resonant circuit includes a radio frequency (RF) micro coil, a capacitor, and a pressure sensing resistor as described in FIG. 4. The RLC circuit may be utilized at the end of an interventional device to make it visible during interventional procedures under MRI guidance. The resonant circuit 603 may be activated by the emitted RF energy of the electromagnetic field produced by the MRI system 601 and various echoing techniques. The high energy field in conjunction with absorption and emission techniques of the MRI system excite the resonant circuit with an RF signal to obtain a tuned RLC circuit to achieve resonance. It is done without any excitation of the RLC circuit from an external source other than the MRI system. The signal (e.g., an RF signal), produced by the resonance circuit is visible in an MR system identifying in the image where the interventional device resides.

The resonant circuit signal may be turned off by detuning the resonant circuit. The detuning is accomplished by changing the value of the resistor thus changing the resonant oscillating frequency of the RLC circuit. The value of the resistor would change, by using a pressure sensor in the resonant circuit, as the pressure in a specialized lumen, such as pressure lumen 408 of FIG. 4, of the device is changed. The pressure changes in this special lumen 604 may be controlled through the proximal end of the catheter by a pressure controller 602. The pressure controller 602 may be a manual device, such as a syringe type inflation device which is coupled to the lumen 604 at a proximal end of the catheter. Alternatively, the pressure controller may be an automated pressure cycling device. This coupled with MRI sequencing techniques to cycle the resonant oscillating frequency on and off would allow for an optimal image of a device markers and the anatomy it was tracking through. The pressure controller may be coupled to the MRI system and may be controlled by the MRI system 601. Alternatively, the pressure controller may be a stand alone component coupled a data processing system. The catheter may be constructed similar to those described in above. It will be appreciated that the circuit 603 is disposed on the catheter or other intervention device and that it will normally be located within the patient's body (e.g. within a coronary artery or other vessel); FIG. 6 diagrammatically shows the circuit 603 outside of the heart in order to show clearly the components of the circuit.

Figure 7:
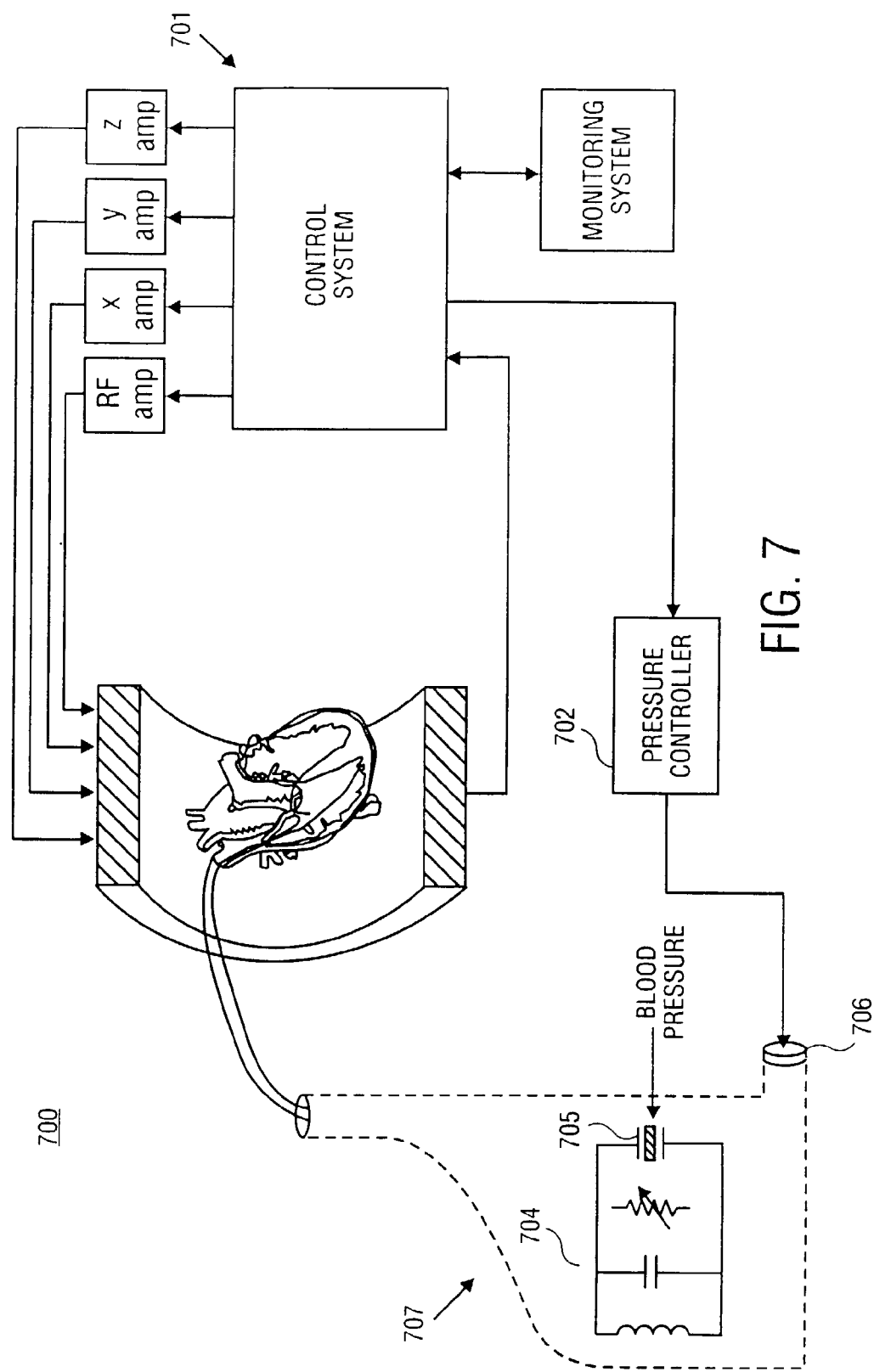
FIG. 7 illustrates yet another alternative system according to an embodiment of the invention.

FIG. 7 illustrates yet a further alternative embodiment of the invention. In this embodiment, a piezoelectric device 705 is employed in a resonant circuit 704. The resonant circuit 704 is excited by the piezoelectric device 705 for tracking interventional devices during MRI guided procedures. The resonant circuit may includes an RF micro coil, a capacitor, a pressure sensitive resistor, and a piezoelectric device, which may be utilized at the end of an interventional device to make it visible during interventional procedures under MRI guidance. The resonant circuit is activated by a hydraulic pressure waveform applied to the piezoelectric component. The hydraulic pressure waveform would also tune the RLC resonant circuit to achieve resonance at the Larmor frequency of the MRI system. The signal (e.g., an RF signal), produced by the resonant circuit is visible in an MRI image identifying in the image where the interventional device resides.

The resonant circuit signal may be turned on and off by changing the frequency of the applied hydraulic pressure signal. The resonant circuit may be tuned or detuned by changing the amplitude of the applied hydraulic pressure signal. The detuning is accomplished by changing the value of the resistor thus changing the resonant frequency of the RLC circuit. The value of the resistor would change, by using a pressure sensor in the resonant circuit, as the pressure in a specialized lumen of the device if changed. The pressure changes in this specialized lumen 706 may be controlled from a proximal end of the device by a pressure controller 702. The pressure controller 702 may be an automated pressure cycling device (e.g., to cause the marker to repeatedly "blink" in the image). Coupling the applied hydraulic pressure signal with the MRI sequencing techniques would allow for an optimal image of a device markers and the anatomy it was tracking through.

Figure 8:
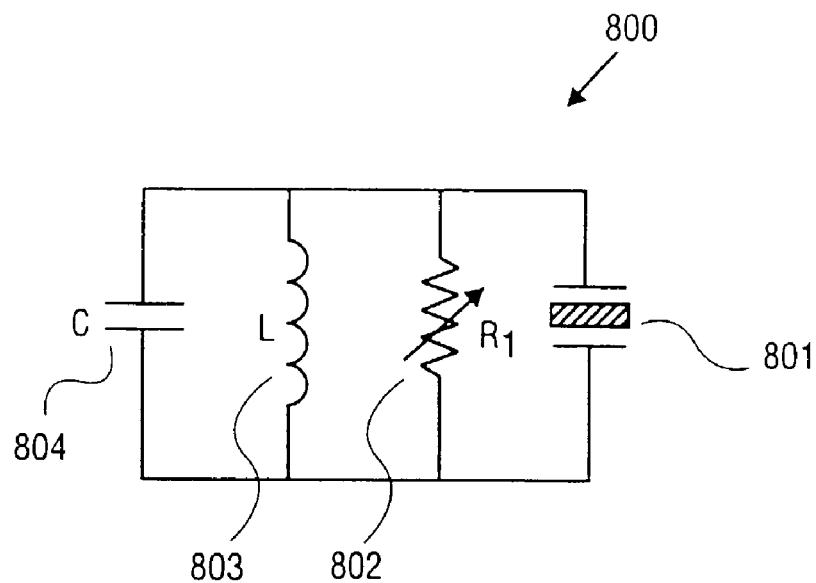
FIG. 8 illustrates yet another alternative catheter according to an embodiment of the invention.
Figure 8:
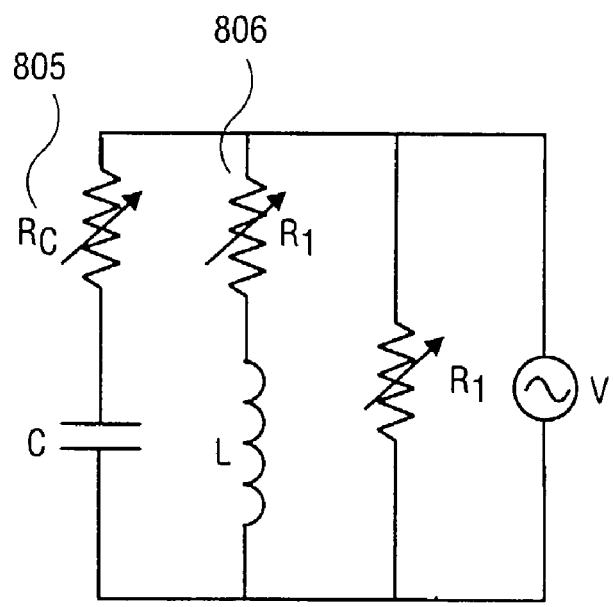

FIG. 8 illustrates an electrical model of the catheter 707 of FIG. 7. The catheter includes an inductor coil 804, a capacitor 803, a pressure sensitive resistor 802, and a piezoelectric device 801. $R_L$ 806 and $R_C$ 805 represent the impedance of inductor 804 and capacitor 803 respectively. When a hydraulic waveform is applied to the piezoelectric device 801, a voltage is generated. The voltage generated causes a current to flow in the resonant circuit 800 and excites the resonant circuit to oscillate at a resonant oscillating frequency determined by the values of RLC. When a hydraulic pressure is applied to the pressure sensing resistor 802, the resonant circuit is tuned or detuned, in and out of a resonant state. Alternatively, the pressure sensitive resistor may receive a pressure from an internal part of a patient's body, such as blood pressure of a human heart. The pressure applied to the piezoelectric device may be different than (or the same as) the pressure applied to the pressure sensitive device. Thus multiple pressure/inflation lumens may provide for separate application of different pressures to the piezoelectric device and the pressure sensitive device or one lumen may apply the same pressure to both devices.

Figure 9:
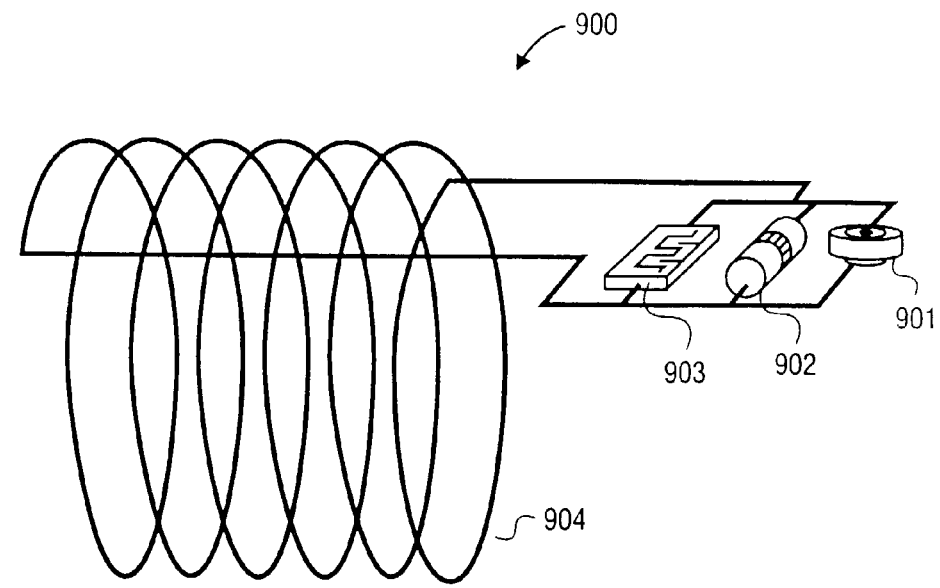
FIG. 9 illustrates yet another alternative catheter according to an embodiment of the invention.
Figure 9:
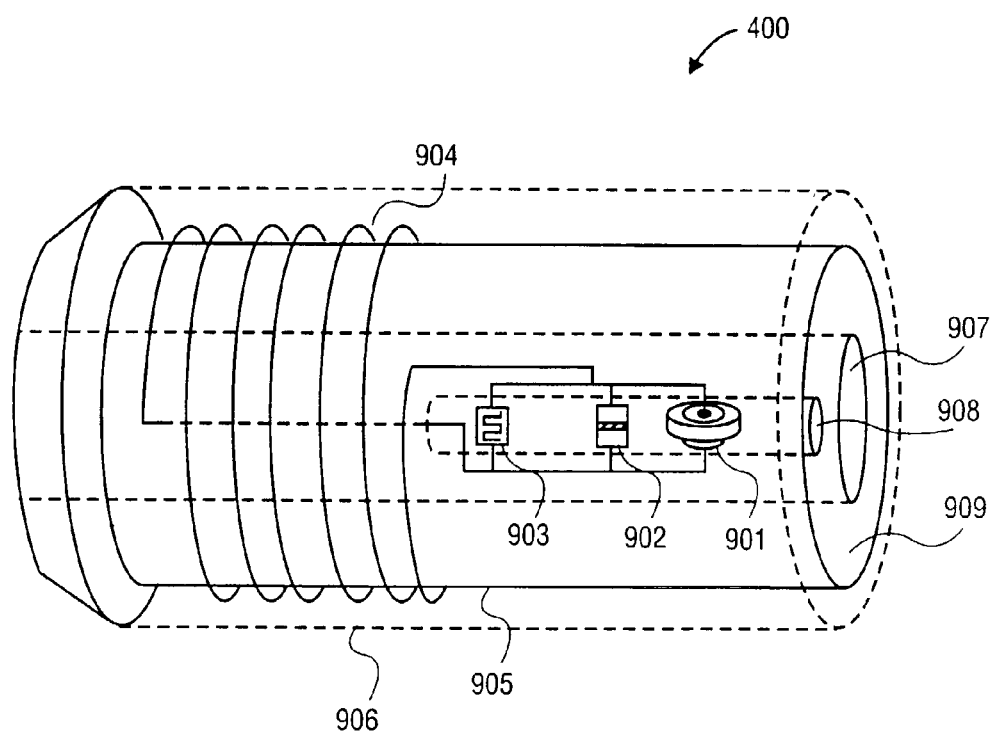

FIG. 9 illustrates another alternative embodiment of a catheter with a resonant circuit built therein. In this embodiment, an LC tank circuit with a pressure sensor resistor 903 and a piezoelectric device 901 is used as a resonant circuit. The pressure sensor 903 may be a miniature pressure sensor for in-vivo measurement of blood pressure. Referring to FIG. 9, the catheter includes an outer member 906 and an inner member 905. The inner member 905 includes a pressure lumen 908, in which a pressure is transmitted to the pressure sensitive resistor 903. The inner member 905 also includes a guide wire lumen 907 where a guide wire may be inserted therethrough. Alternatively, the pressure sensitive resistor 903 may receive pressure from a blood pressure, such as blood pressure 204 from a human heart 202 of FIG. 2.

In one embodiment, the miniature pressure sensing resistor may be applied to the catheter in a subminiature substrate form and doped, applied with adhesive to the wall of the catheter tubing, or incorporated into the wall of the tubing 909. The outputs of the miniature pressure sensing resistor are attached to the capacitor and inductor micro coil circuit in a parallel or series configuration. The micro coil 904 may be wound around the tubing or positioned on the device in a fashion, which facilitates the highest Q factor possible. The tubing can contain or have incorporated into its lumen or wall signal enhancing material. The capacitor may be a small surface mount capacitor available in the art. Alternatively, it can be fashioned into the wall of the tube by such means as conductive metal films and non-conductive polymer layers. The piezoelectric device 901 may be attached to the resonant circuit to provide electrical excitation. Communication between the piezoelectric device and the miniature pressure sensing resistor 903 and the proximal pressure controller is maintained through a pressure lumen 908 of the device. The communication may be achieved through a guide wire lumen 907, an inflation lumen such as inflation lumen 507 of FIG. 5B, or through a special hydraulic communication lumen 908.

In an alternative embodiment, more than one micro coils may be used to create a multi-marker catheter. This multi-marker configuration would be electrically wired the same as the single coil circuit, however, it may be separated by the capacitor in series with the micro coils and in parallel with the miniature pressure sensing resistor.

Figure 10:
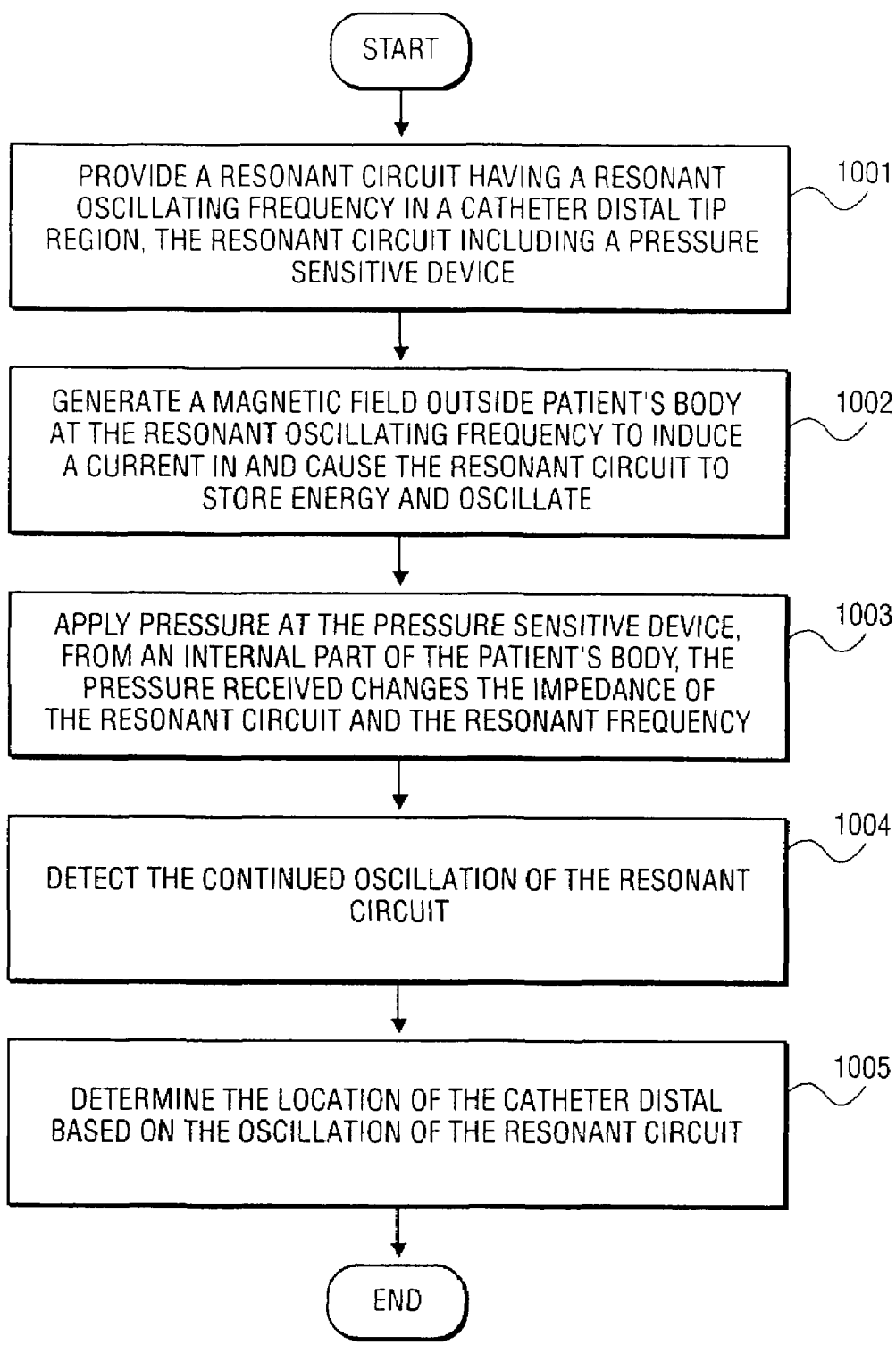
FIG. 10 illustrates a flowchart of a method for locating a catheter according to one embodiment of the invention.

FIG. 10 illustrates an exemplary method for locating an active marker according to an embodiment of the invention. The method includes providing a pressure sensitive device attached to a body of a catheter, providing a resonant circuit coupled to the pressure sensitive device in the catheter, the resonant circuit having a resonant oscillating frequency, generating a magnetic field (for example, at the resonant oscillating frequency), the magnetic field inducing and causing the resonant circuit to oscillate, applying a pressure on the pressure sensitive device, the pressure applied on the pressure sensitive device changing the resonant frequency of the resonant circuit, detecting the oscillation of the resonant circuit, and determining location of the catheter based on the oscillation of the resonant circuit.

Referring to FIG. 10, at block 1001, the method includes providing a resonant circuit having a resonant oscillating frequency in a catheter distal tip region, the resonant circuit including a pressure sensitive device. In one embodiment, the resonant circuit includes a tank LC circuit. The values of the LC are adjusted to have a predetermined oscillating frequency, such as the frequency used by an ordinary MRI system. The LC circuit is excited by an MRI system and oscillates at a resonant frequency set by the LC values. The pressure sensitive device may be a pressure sensitive resistor. The resistant value changes depending upon the pressure applied to the pressure sensitive resistor. The interventional device with the resonant circuit (e.g. a catheter with the circuit near a distal end of the catheter) is introduced into the patient's body. Next, at block 1002, the method generates a magnetic field outside patient's body at the resonant oscillating frequency to induce a current in and cause the resonant circuit to store energy and oscillate. In one embodiment, the magnetic field is generated through an ordinary MRI system well known in the art. After the magnetic field is generated, the resonant circuit oscillates. At block 1003, the pressure sensitive device receives a pressure from an internal part of the patient's body, and the pressure received changes the impedance of the resonant circuit. In one embodiment, the pressure received comes from a blood pressure of a blood vessel of a patient. As a result, the resonant frequency of the circuit has been changed. When the resonant circuit oscillates, the circuit generates a radio frequency (RF) signal as an image of itself. At block 1004, the image generated from the oscillation of the resonant circuit is detected and received by a transceiver of an input system. In one embodiment, the input system is part of an ordinary MRI system, which is well known to the art. Based on the images received from the oscillation of the resonant circuit, at block 1005, the system determines the location of the catheter distal tip. The system receiving the image of the catheter distal tip may be part of the data processing system of an MRI system. In an alternative embodiment, the data processing system may be a separate data processing system communicating with an MRI system.

Figure 11:
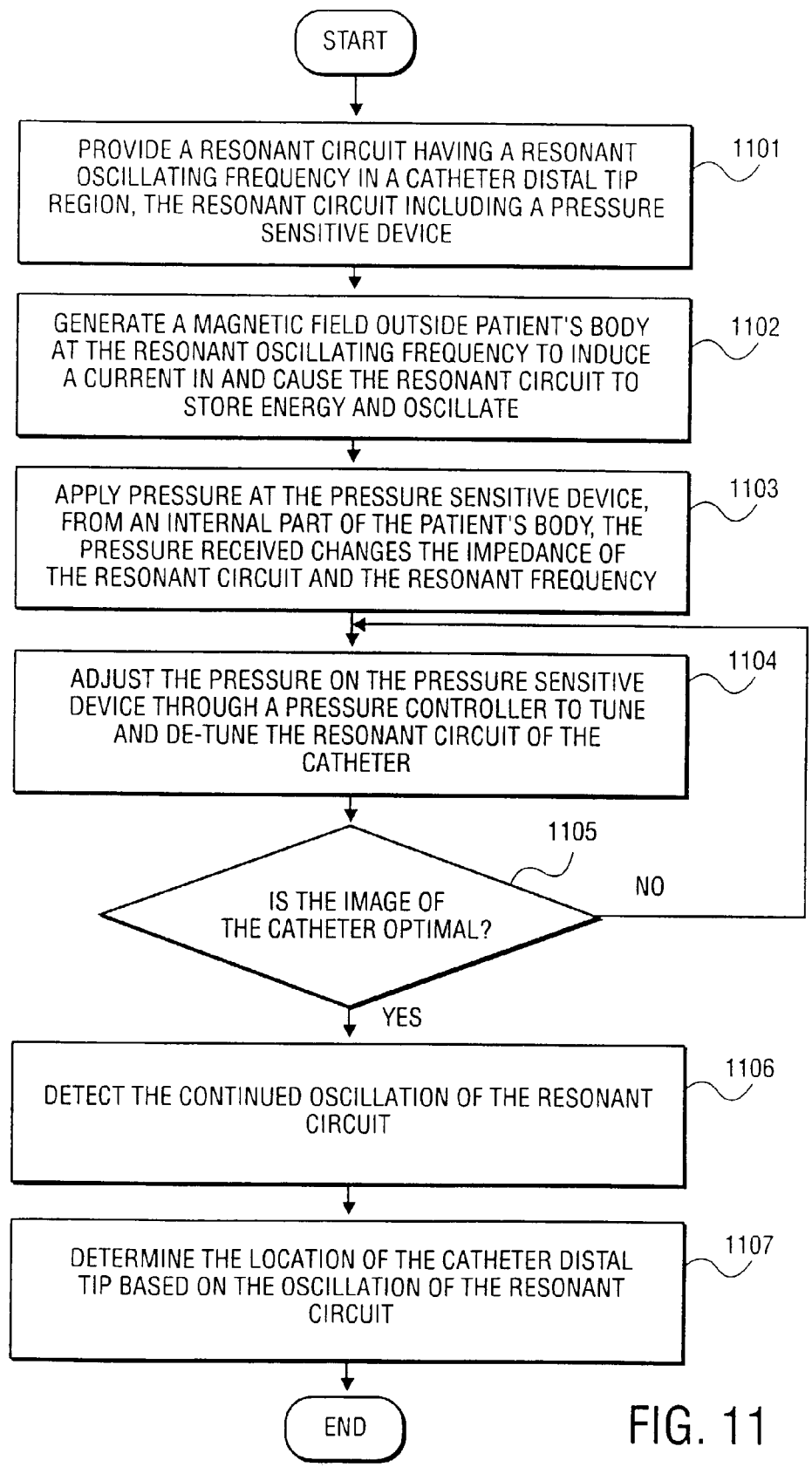
FIG. 11 illustrates an alternative flowchart of a method for locating a catheter according to one embodiment of the invention.

FIG. 11 illustrates an alternative embodiment of the invention, wherein the pressure applied on the pressure sensitive device is received from an external pressure source through a pressure controller. Referring to FIG. 11, at operation block 1101, a resonant circuit is provided, the resonant circuit having a pressure sensitive device. The resonant circuit has a resonant oscillating frequency determined by the components of the resonant circuit. In one embodiment, the resonant circuit may be attached in the outer wall of a catheter distal tip region which is introduced into a patient's body. In an alternative embodiment, the resonant circuit may be incorporated into the body of the catheter distal tip region which is introduced into a patient's body. The pressure sensitive device changes the impedance of the device upon a pressure is applied to the device. In one embodiment, the pressure sensitive device includes a pressure sensitive resistor, where the resistance of the device changes depending on the pressure applied to the device.

At block 1102, a magnetic field is generated outside the patient's body. In one embodiment, the magnetic field is generated from an ordinary magnetic resonant imaging (MRI) system. Typically, the magnetic field is generated at a resonant oscillating frequency to induce and cause the resonant circuit to store energy and oscillate. It is preferred that the resonant oscillating frequency of the magnetic field is substantially matched to the resonant oscillating frequency of the resonant circuit of the catheter. When the magnetic field is radiated and applied to the resonant circuit, the resonant circuit oscillates at a resonant oscillating frequency determined by the values of the components of the resonant circuit. It would be appreciated that, in one embodiment, the values of the components of the resonant circuit are tuned to have a resonant oscillating frequency substantially close to the Larmore frequency used by the MRI system. As a result, the resonant circuit generates a radio frequency (RF) signal which may be detected and captured by a receiving system, such as an ordinary MRI system.

After the RF signal is generated and applied to the resonant circuit, at block 1103, a pressure is applied to the pressure sensitive device, such as pressure sensitive resistor, from an external pressure source. In one embodiment, the pressure is generated and applied through an external pressure controller which may be coupled to an inflation lumen at a proximal end of a catheter, for example. Upon receiving the pressure, the pressure sensitive device changes its resistance value, as a result. As described above, the resonant oscillating frequency of the resonant circuit, in one embodiment is determined in part by the impedance of the resonant circuit. When the pressure is applied to the pressure sensitive device, the impedance of the pressure sensitive device changes, which in turn changes the impedance of the resonant circuit. As a result, the resonant oscillating frequency of the resonant circuit changes, which in turn tunes and detunes the resonant circuit in and out of the resonant oscillating state. Thus the RF signal generated from the resonant oscillation of the resonant circuit changes, from which the receiving system (e.g., MRI system) can detect the location of the distal portion of the catheter. For example, a periodic tuning and detuning of the circuit can cause a marker, produced by the circuit, to blink on an MRI image.

At block 1104, the pressure applied to the pressure sensitive device may be adjusted through a pressure controller to tune and detune the resonant circuit inside the distal portion of the catheter. It is useful to note that, by adjusting the pressure applied to the pressure sensitive device, the resonant oscillation of the resonant circuit may be tuned to an optimal state such that an optimal image of the distal portion of the catheter may be received. The pressure controller may be adjusted manually. Alternatively, the pressure controller may be an automatic pressure controller coupled to an MRI system. At block 1105, when the image of the distal portion of the catheter is received at an MRI system, the MRI system may check whether the image of the catheter is optimal. The MRI system then may communicate with the pressure controller to adjust the pressure applied to the pressure sensitive device of the resonant circuit until an optimal image is received.

At block 1106, the resonant oscillation of the resonant circuit is then detected through a receiving system, such as an MRI system, based on the RF signal generated through the resonant oscillation of the resonant circuit. At block 1107, based on the image of the oscillation of the resonant circuit inside the distal portion of the catheter, the location of the distal portion of the catheter is determined.

Figure 12:
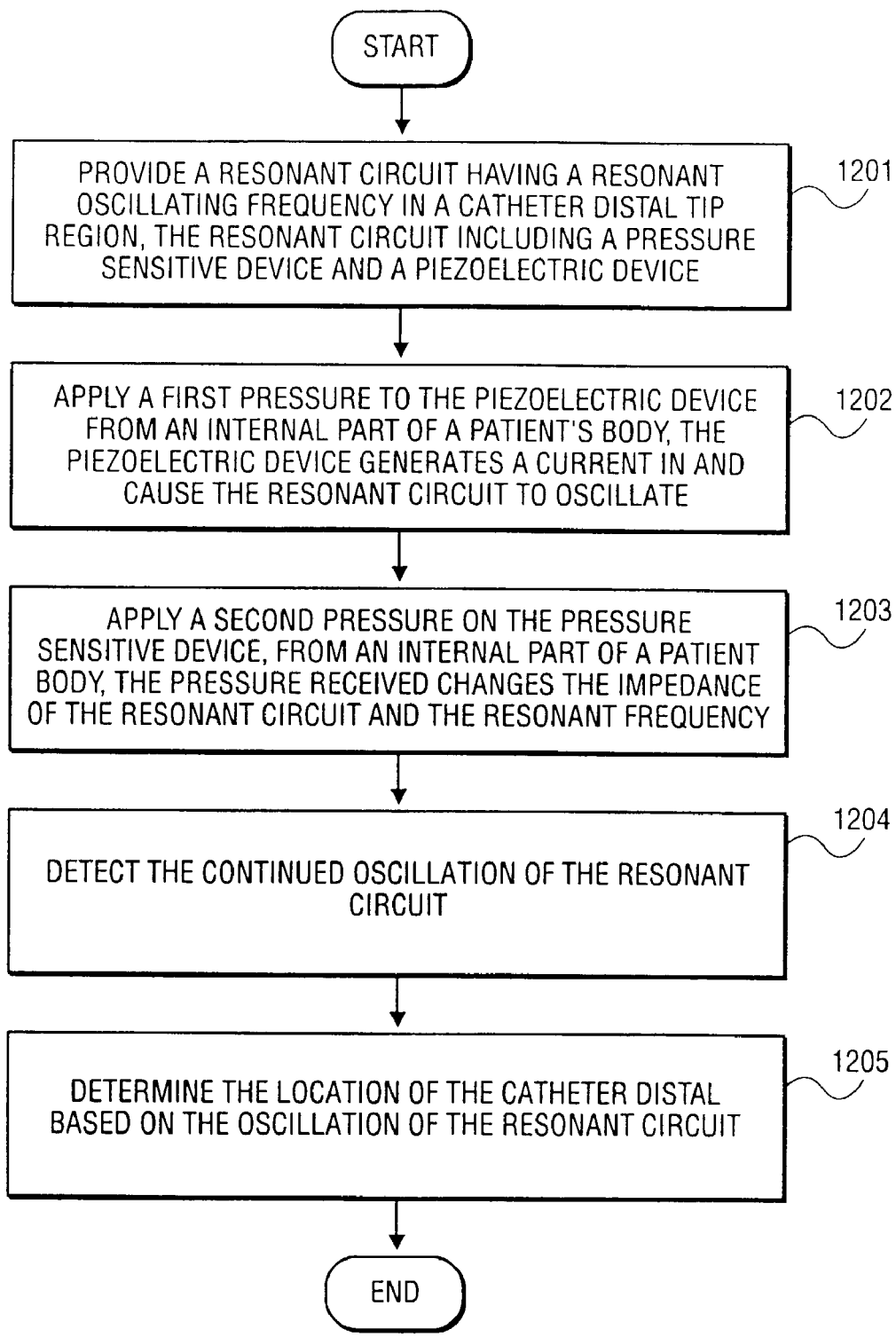
FIG. 12 illustrates yet another alternative flowchart of a method for locating a catheter according to one embodiment of the invention.

FIG. 12 illustrates yet another aspect of the invention according to one embodiment. The method of FIG. 12 includes providing a pressure sensitive device and a piezoelectric device attached to a body of a catheter, providing a resonant circuit coupled to the pressure sensitive device and the piezoelectric device in the catheter, the resonant circuit having a resonant oscillating frequency, applying a first pressure on the piezoelectric device, the first pressure applied on the piezoelectric device causing the piezoelectric device to generate a current in and cause the resonant circuit to oscillate, applying a second pressure on the pressure sensitive device, the second pressure applied on the pressure sensitive device changing the resonant frequency of the resonant circuit, detecting the oscillation of the resonant circuit, and determining location of the catheter based on the oscillation of the resonant circuit.

Referring to FIG. 12, at block 1201, a resonant circuit having a resonant oscillating frequency in a catheter distal tip region is provided. The resonant circuit includes a pressure sensitive device and a piezoelectric device. In one embodiment, the pressure sensitive device may be a pressure sensitive resistor, where the resistance changes based on the pressure received. At block 1202, the piezoelectric device receives a first pressure from an internal part of a patient's body. In one embodiment, the pressure is received from a blood pressure of the patient's body. Upon receiving the pressure the piezoelectric device generates a current flowing in the resonant circuit and cause the resonant circuit to oscillate. In this embodiment, the resonant circuit is normally activated by the piezoelectric device when a pressure is received. There is no external source to activate the resonant circuit in this embodiment.

At block 1203, the pressure sensitive device, such as pressure sensitive resistor, receives a second pressure from an internal part of a patient's body. The pressure may be received from a blood pressure of the patient's body. As described above, the pressure received changes the impedance of the pressure sensitive device, which in turn changes the impedance of the resonant circuit. As a result, the resonant oscillating frequency of the resonant circuit is changed accordingly. Thus, the resonant circuit may be tuned or detuned in and out of a resonant state, and at block 1204, such oscillation may be detected. Consequently, the image of the resonant circuit may be displayed in a flashing fashion in a display device, from which, at block 1205, the location of the resonant circuit inside the distal portion of the catheter may be detected accordingly.

The pressure received may come as a pressure wave generated from an internal part of a patient's body, such as a blood vessel. The pressure wave may be transformed synchronously with the heartbeat of the patient. As a result, the current generated in the resonant circuit may change dynamically with respect to the pressure wave received. The dynamic changes of the current flowing in the resonant circuit cause the resonant circuit to be tuned or detuned at the resonant frequency, preferably at Larmore frequency. Thus, according to one embodiment of the invention, the image of the resonant circuit located at the distal end of the catheter may be received and displayed by the MRI system in a flashing manner. Accordingly, the location of the distal end of the catheter is determined.

Figure 13:
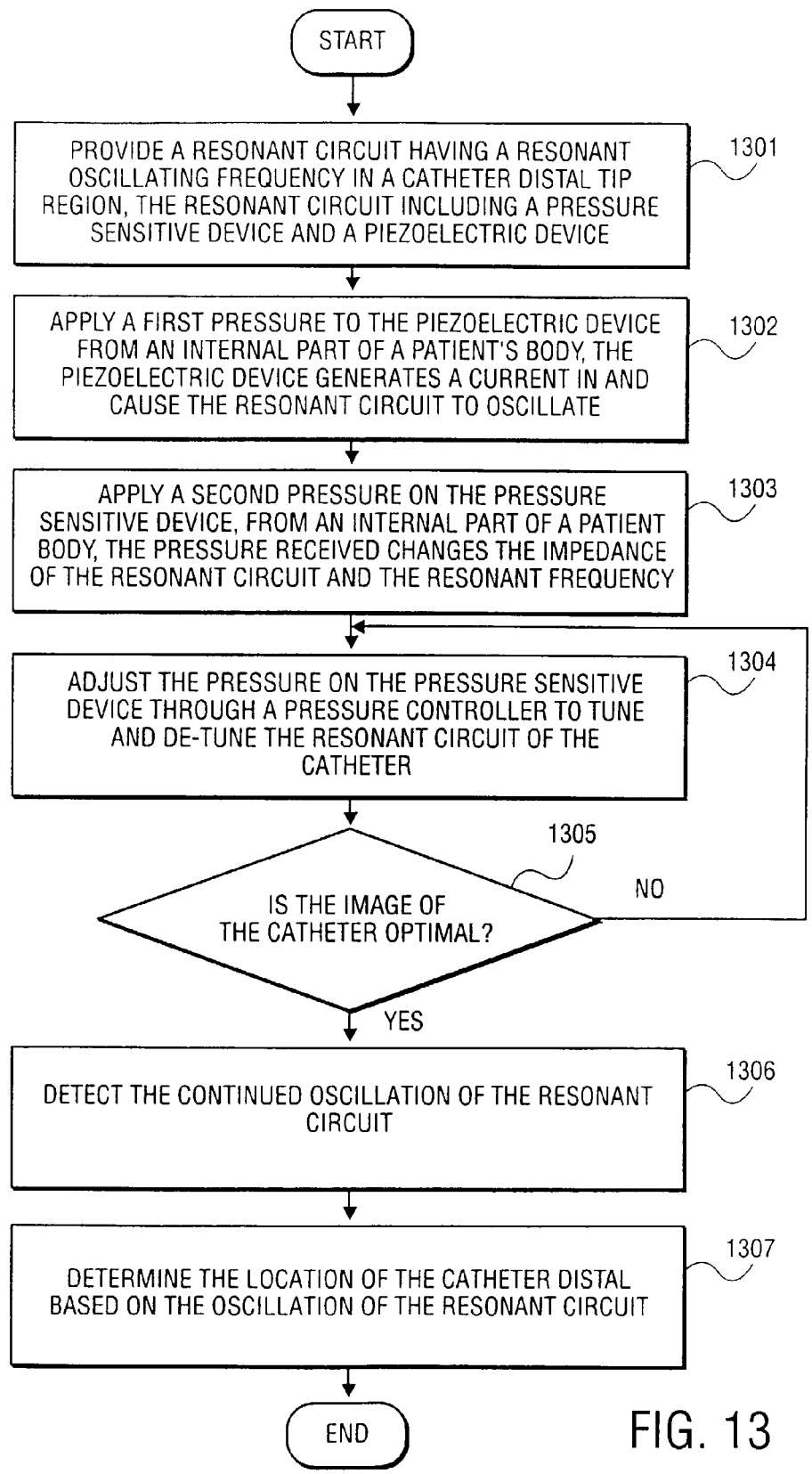
FIG. 13 illustrates an alternative flowchart of a method for locating a catheter according to one embodiment of the invention.

FIG. 13 illustrates yet another alternative embodiment of the present invention. In this embodiment, the pressure received at the pressure sensitive device may be generated from an external pressure controller, such as, for example, a controller, at a proximal end, coupled to a hydraulic control lumen which transmits the pressure from the controller to the pressure sensitive device at the distal end). The pressure controller may generate pressure manually. Alternatively, the pressure controller may be controlled by a data processing system communicating with an MRI system. Referring to FIG. 13, at block 1301, a resonant circuit is provided, the resonant circuit having a resonant oscillating frequency in a catheter distal tip region. In one embodiment, the resonant circuit may be an LC tank circuit. The resonant circuit includes a pressure sensitive device and a piezoelectric device. The pressure sensitive device may be a pressure sensitive resistor. At block 1302, the piezoelectric device receives a first pressure from an internal part of a patient's body. Upon receiving the first pressure, the piezoelectric device generates a current in the resonant circuit, which activates the resonant circuit. The current activating the resonant circuit causes the resonant circuit to oscillate at a resonant oscillating frequency. The resonant oscillating frequency is determined by the component of the resonant circuit. In a case of an LC resonant circuit, the resonant oscillating frequency is determined mainly by the value of the inductor and capacitor, as well as the impedance of the resonant circuit. In this embodiment, the impedance of the resonant circuit relates to the impedance of the pressure sensitive device (e.g., resistance of the pressure sensitive resistor). The resonant circuit in one embodiment which uses a piezoelectric device, is completely activated and excited through the internal component of the circuit (e.g., piezoelectric device), without any external activation source. This is unlike a conventional method which employs an external source to activate the resonant circuit, which may cause harm to the patient when the external source heats up the circuit.

At block 1303, the pressure sensitive device receives a second pressure from an external source to tune and detune the resonant circuit of the catheter. The pressure applied to the pressure sensitive device may be generated through a pressure controller. The pressure controller may be coupled to a data processing system of an MRI system. The image of the resonant circuit inside the distal tip region of a catheter is received at an MRI system. The MRI system checks the image, at block 1305, whether the image is at an optimal state. The MRI may instruct the pressure controller to adjust 1304 the pressure applied to the pressure sensitive device to tune and detune the resonant circuit in and out of the resonant state, until the oscillation of the resonant circuit is detected, at block 1306. Based on the oscillation of the resonant circuit, at block 1307, the location of the resonant circuit inside the distal tip region of a catheter is determined.

Figure 14A:
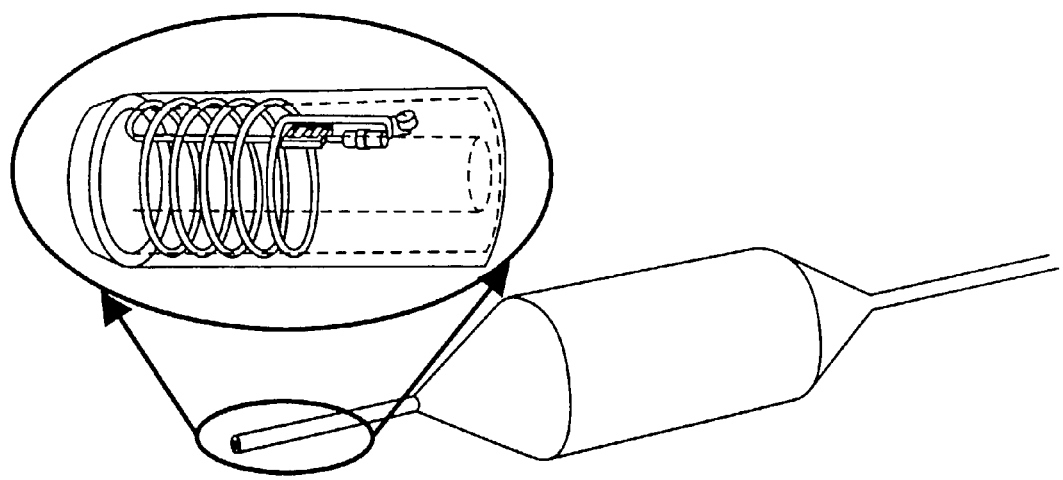
FIGS. 14A and 14B illustrate a preferred embodiment of a catheter of the present invention.
Figure 14A:
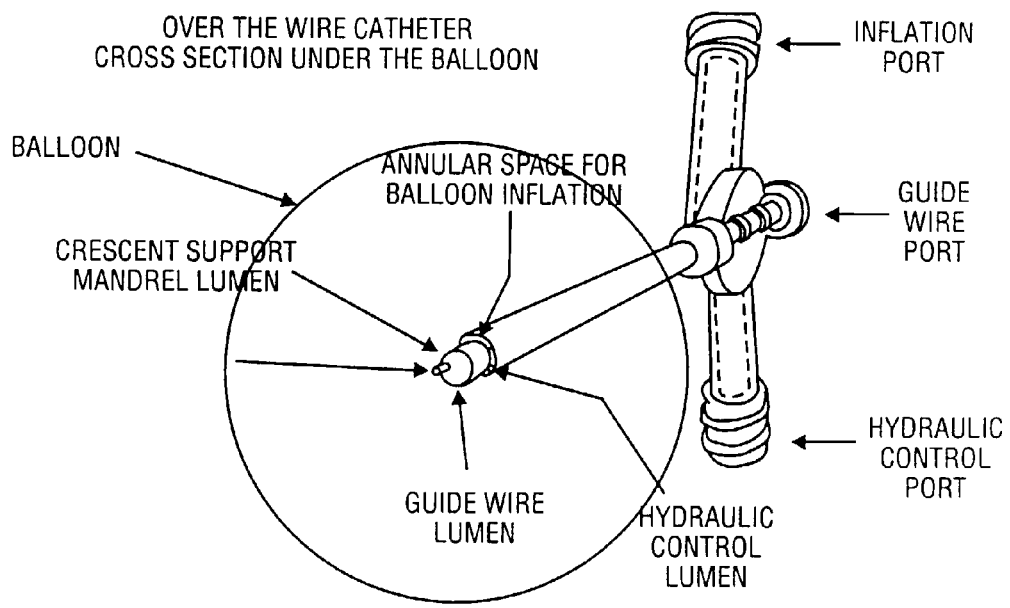
Figure 14B:
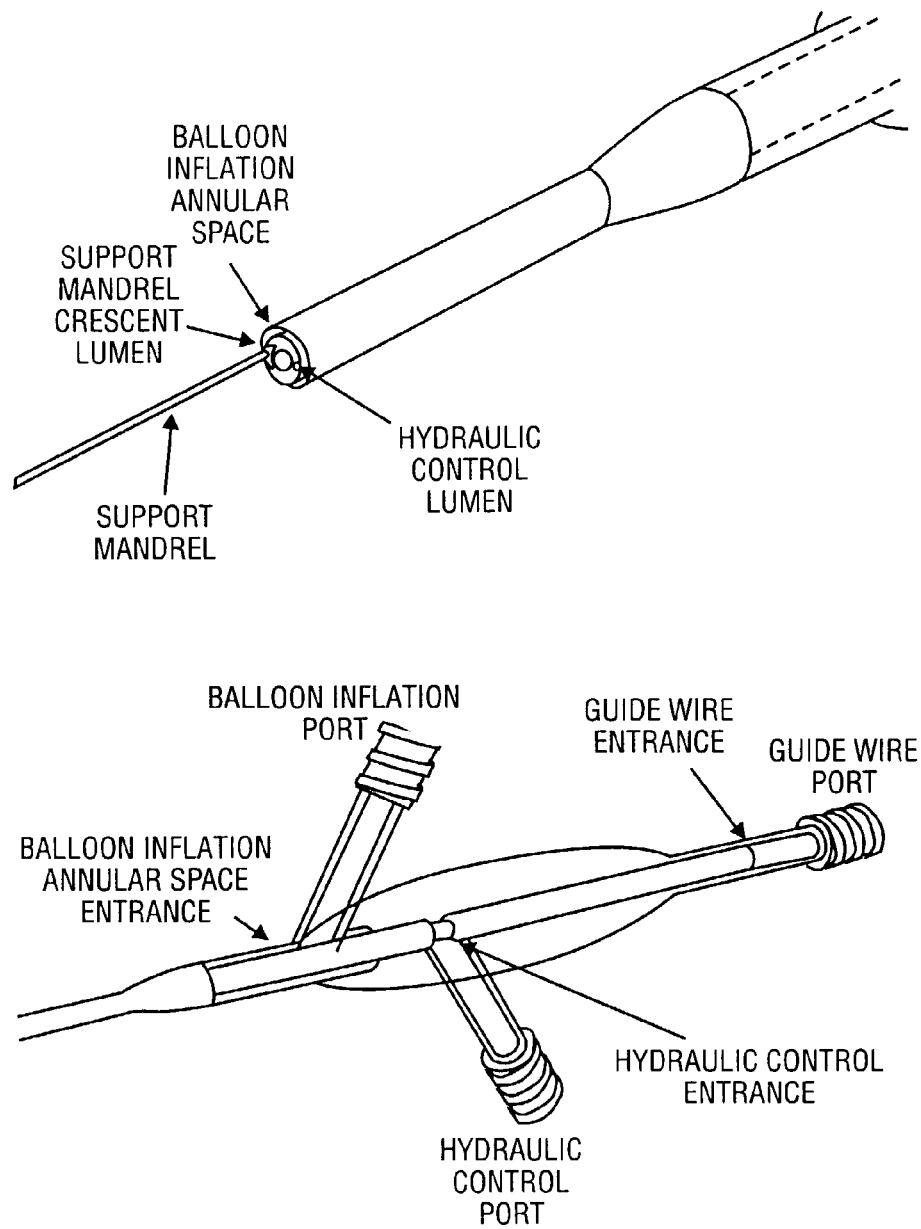

FIGS. 14A and 14B illustrate an exemplary embodiment of a catheter according to an aspect of the invention.

It will be appreciated that the various markers described herein may be used with a variety of different medical intervention devices. For example, these various markers may be used in balloon angioplasty catheters or guidewire catheters or stent delivery catheters or drug delivery catheters or radiation delivery catheters, etc. These various catheters will often include numerous lumens such as guidewire lumen, a balloon inflation lumen (e.g. to inflate an angioplasty or centering balloon), a perfusion lumen, a drug delivery lumen, etc. In addition, in those embodiments which use an external pressure controller, an additional lumen, such as an hydraulic pressure lumen (to transmit a pressure from the controller with a proximal end of the catheter to a pressure sensitive device at a distal end), is included in such catheters. Other types of medical intervention devices may use the various markers described herein.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for locating a catheter, the method comprising:
   providing a pressure sensitive device attached to a body of a catheter;
   providing a circuit coupled to the pressure sensitive device in the catheter,
   generating a magnetic field, the magnetic field inducing and causing the circuit to oscillate;
   applying a pressure on the pressure sensitive device, the pressure applied on the pressure sensitive device changing an oscillating frequency of the circuit;
   detecting oscillation of the circuit; and
   determining location of the catheter based on the oscillation of the circuit.

2. The method of claim 1, wherein the pressure sensitive device is attached to an outer wall of the catheter.

3. The method of claim 1, wherein the pressure sensitive device is incorporated into a wall of the catheter.

4. The method of claim 1, wherein the circuit is located at a distal tip region of the catheter.

5. The method of claim 1, wherein the circuit comprises an LC circuit incorporated into a tip structure of the catheter.

6. The method of claim 5, wherein the LC circuit comprises:
   a capacitor;
   an inductor coil coupled to the capacitor in parallel or in series; and
   wherein the inductor coil is wound around the catheter in a way such that the circuit contains a maximum Q factor.

7. The method of claim 6, wherein the LC circuit comprises multiple inductor coils.

8. The method of claim 7, wherein the multiple inductor coils are separated by capacitors coupled in series or in parallel.

9. The method of claim 1, wherein the magnetic field is generated through a magnetic resonant image (MRI) system.

10. The method of claim 1, wherein the pressure applied on the pressure sensitive device is received from an internal part of a patient's body.

11. The method of claim 10, wherein the pressure applied on the pressure sensitive device is received from a blood pressure of the patient's body.

12. The method of claim 1, wherein the pressure applied on the pressure sensitive device is received from an external pressure source through a pressure controller.

13. The method of claim 12, further comprising adjusting the pressure applied on the pressure sensitive device through the pressure controller, such that the circuit is operating in and out of a resonant state.

14. The method of claim 1, wherein the pressure sensitive device is a pressure sensitive resistor, wherein the resistance of the pressure sensitive resistor changes based on the pressure applied on the pressure sensitive resistor.

15. The method of claim 1, further comprising:
   generating a radio frequency (RF) signal through the oscillation of the circuit;
   detecting the oscillation of the circuit through sensing the intensity of the RF signal; and
   determining the location of the catheter distal tip based on signals produced through the RF signal.

* * * * *